United States Patent [19]  [11] 4,202,977
Irikura et al.  [45] May 13, 1980

[54] S-TRIAZOLO [1,5-A] PYRIDINE DERIVATIVES

[75] Inventors: Tsutomu Irikura, Tokyo; Seigo Suzue, Kuki, both of Japan

[73] Assignee: Kyorin Pharmaceutical Co., Ltd., Tokyo, Japan

[21] Appl. No.: 15,590

[22] Filed: Feb. 27, 1979

[51] Int. Cl.² .......................................... C07D 471/04
[52] U.S. Cl. .................................... 544/362; 546/119
[58] Field of Search ........................ 544/362; 546/119

[56] References Cited

U.S. PATENT DOCUMENTS

| | | | |
|---|---|---|---|
| 3,472,853 | 10/1969 | Archer | 544/362 |
| 3,956,328 | 5/1976 | Irikura | 544/362 |

*Primary Examiner*—Paul M. Coughlan, Jr.
*Attorney, Agent, or Firm*—Armstrong, Nikaido, Marmelstein & Kubovcik

[57] ABSTRACT

This invention relates to new compounds of value as antihypertensives.
More particularly, it relates to s-triazolo [1,5-a] pyridine derivatives and the acid addition salts thereof.

11 Claims, No Drawings

S-TRIAZOLO [1,5-A] PYRIDINE DERIVATIVES

SUMMARY OF THE INVENTION

This invention relates to new compounds of value as antihypertensives and more particularly to new s-triazolo[1,5-a]pyridine derivatives and pharmacologically acceptable acid addition salts.

DETAILED DESCRIPTION OF THE INVENTION

The novel s-triazolo[1,5-a]pyridine derivatives of the present invention can be represented by the general formula (I),

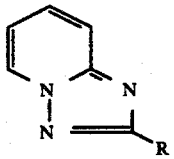

(I)

wherein R represents —CH=N—R$^1$ (wherein R$^1$ represents dimethylamino), and

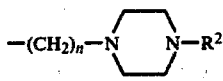

(wherein R$^2$ represents phenyl, 2-methoxyphenyl, benzyl, 2-chlorobenzyl and 2-pyridyl, and n represents 3 and 5).

The novel compounds of the present invention can be prepared by the following procedures.

The compounds represented by the general formula (I), wherein R represents —CH=N—R$^1$, in which R$^1$ has the value noted above, can be prepared by reacting 2-dihalogenomethyl-s-triazolo[1,5-a]pyridine with the corresponding substituted hydrazine in the solvent such as, for example, dimethylformamide and so on, and preferably in the presence of a base such as, for example, potassium carbonate and so on.

2-dihalogenomethyl-s-triazolo[1,5-a]pyridine of starting compound can be prepared by reacting 1,2-diaminopyridinium iodide with methyl dihalogenoacetate.

The compounds represented by the general formula (I), wherein R represents

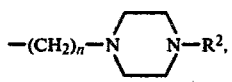

in which —R$^2$ and n have the value noted above, can be prepared by reacting a compound having the general formula (II),

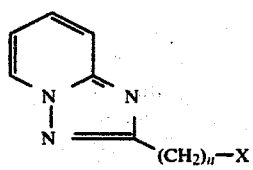

(II)

wherein X represents halogen and n has a value noted above, with a compound having the general formula (III),

(III)

wherein R$^2$ has the value noted above, in the solvent such as, for example, ethanol, dimethylformamide, toluene and so on, and preferably in the presence of equimolar or more amount of a base such as, for example, potassium carbonate, triethylamine and so on at a temperature near the boiling point of the used solvent.

The following examples serve to illustrate the invention.

Example for reference (1) 2-Dichloromethyl-s-triazolo[1,5-a]pyridine

A solution of 24 g of 1,2-diaminopyridinium iodide and 6.6 g. of sodium hydroxide in 200 ml of ethanol was stirred at 50°–60° C. for 1 hour. To the reaction mixture was added 17.2 g of methyl dichloroacetate and the mixture was refluxed with stirring for 4 hours. The mixture was concentrated under reduced pressure, water was added and extracted with chloroform.

The chloroform layer was concentrated to give crude crystalline product, which was recrystallized from 60 ml of benzene. Colorless needles, mp 133°–134° C., 16.8 g were obtained. Anal. Calcd. for C$_7$H$_5$N$_3$Cl$_2$: C, 41.61; H, 2.49; N, 20.80. Found: C, 41.91; H, 2.55; N, 20.83.

(2) 2-(3-Chloropropyl)-s-triazolo[1,5-a]pyridine (A) A mixture of 24 g of 1,2-diaminopyridinium iodide, 17.2 g of γ-butyrolactone and 57 g of potassium carbonate in 100 ml of diethylcellosolve was refluxed with stirring for 8 hours. The mixture was concentrated under reduced pressure to the residue, which was extracted by hot dichloromethane. The solvent was removed to give crude 2-(3-hydroxypropyl)-s-triazolo[1,5-a]pyridine, which was recrystallized from ethyl acetate to colorless needles (16 g, 90%), mp 71.5°–73° C. Anal. Calcd. for C$_9$H$_{11}$ON$_3$: C, 61.00; H, 6.24; N, 23.72. Found: C, 60.82; H, 6.14; N, 23.48.

(B) To 50 ml of phosphorus oxychloride was added gradually 34.5 g of 2-(3-hydroxypropyl)-s-triazolo[1,5-a]pyridine. After the addition was completed, the mixture was warmed on water bath at 90°–95° C. for 30 min., cooled and poured onto cracked ice. The mixture was neutralized with potassium carbonate and extracted with chloroform. The chloroform layer was dried over anhydrous sodium sulfate and concentrated to give crude product, which was recrystallized from cyclohexane as colorless needles (22.5 g, mp 56.5°–57° C.). Anal. Calcd. for C$_9$H$_{10}$N$_3$Cl: C, 55.25; H, 5.15; N, 21.48. Found: C, 55.21; H, 5.20; N, 21.55.

(3) 2-(5-Chloropentyl)-s-triazolo 1.5-a pyridine

In the same manner as shown in Example for reference (2), part A and B, the compound was prepared by using -caprolactone with 45% total yield and obtained as an oil, of which picrate melts at 136°–137° C. Anal. Calcd. for C$_{11}$H$_{14}$N$_3$Cl.C$_6$H$_3$O$_7$N$_3$: C, 45.09; H, 3.78; N, 18,56. Found: C, 43.39; H, 3.36; N, 18.75.

Example 1.

2-(N,N-Dimethylhydrazonomethyl)-s-triazolo-1,5-a pyridine

A mixture of 11.0 g of 2-dichloromethyl-s-triazolo-1,5-a pyridine, 7.6 g of potassium carbonate, 300 mg of sodium iodide and 12 g of N,N-dimethylhydrazine in 160 ml of dimethylformamide was refluxed for 12 hours under stirring. The solvent was removed under reduced pressure and to the residue 200 ml of water saturated with sodium chloride was added. The mixture was extracted with chloroform. The extracts were concentrated and the residue was recrystallized from benzene-n-hexane to give colorless crystals (5.6 g, mp 132°–133° C.). Anal. Calcd. for $C_9H_{11}N_5$: C, 57.12; H, 5.86; N, 37.02. Found: C, 57.18; H, 5.97; N, 37.19.

Example 2.

2-[3-(4-Phenylpiperazino)propyl]-s-triazolo[1,5-a]pyridine

A solution of 5.7 g of 2-(3-chloropropyl)-s-triazolo[1,5-a]pyridine, 5.2 g of 1-phenylpiperazine and 10 ml of triethylamine in 140 ml of dimethylformamide was refluxed for 10 hours. The reaction mixture was concentrated under reduced pressure and to the residue 1 N-aqueous sodium hydroxide (50 ml) was added. The mixture was extracted with chloroform and the extracts were concentrated to give crude product, which was purified by alumina column chromatography to obtain 7.1 g of oily product. The oily product was converted to the salt of maleic acid by usual way. The maleate was recrystallized from ethanol-petroleum ether (10:4) to colorless prisms, mp 167.5°–168.5° C. Yield was 50%.

Anal. Calcd. for $C_{19}H_{23}N_3 \cdot C_4H_4O_4$: C, 63.14; H, 6.22; N, 16.01. Found: C, 63.03; H, 6.22; N, 16.14.

Example 3.

2-[3-(4-o-Methoxyphenylpiperazino)propyl]-s-triazolo[1,5-a]pyridine

A solution of 3.9 g of 2-(3-chloropropyl)-s-triazolo[1,5-a]pyridine, 3.8 g of 1-o-methoxyphenylpiperazine and 2.8 g of potassium carbonate in 150 ml of dimethylformamide was refluxed for 8 hours. Then the reaction mixture was proceeded by the same manner as described in Example 2. The compound was recrystallized from cyclohexane to give colorless prisms, mp 55°–55.5° C. Yield was 60%. Anal. Calcd. for $C_{20}H_{25}ON_5$: C, 68.35; H, 7.17; N, 19.53. Found: C, 68.20; H, 6.94; N, 20.21.

The compounds of the following examples 4 to 8 were prepared by the same manner as shown in Example 3.

| Example No. | n | R² | Yield (%) | mp (°C.) | Recryst. solvent | Analysis Calcd. C | H | N |
|---|---|---|---|---|---|---|---|---|
| | | | | | | Found. C | H | N |
| 4 | 3 | —CH₂—C₆H₅ | 40 | picrate 234–236 | E*¹ | 48.43 | 3.94 | 19.41 |
| | | | | | | 48.37 | 4.10 | 19.39 |
| 5 | 3 | —CH₂—C₆H₄Cl | 57 | maleate 172–173 | E | 55.85 | 5.36 | 11.63 |
| | | | | | | 55.85 | 5.56 | 11.42 |
| 6 | 3 | pyridyl | 42 | 77.5 | C*² | 67.05 | 6.88 | 26.07 |
| | | | | | | 67.09 | 6.84 | 25.99 |
| 7 | 5 | phenyl | 56 | oil*³ | | | | |
| 8 | 5 | —C₆H₄—OCH₃ | 60 | oil*⁴ | | | | |

*¹E: ethanol
*²C: cyclohexane
*³Structural proof was made by mass spectral analysis. m/e 349 (M⁺).
*⁴Structural proof was made by mass spectral analysis. m/e 379 (M⁻).

The antihypertensive effect of the compounds of this invention is given in Table.

Blood pressure was determined under the unanesthetized and unrestrained conditions in spontaneously hypertensive rats (SH rat) which had been implanted chronically with a cannula into the femoral vein. Results are presented as the mean decreased percent in blood pressure determined at 15, 30, 60, 120 and 180 minutes after intraperitoneal (i.p.) or oral (p.o) administration of the test compounds.

The compounds of this invention showed more potent antihypertensive effect in SH rats as compared with the reference drugs, then are promising as antihypertensive drugs.

Table

| | Antihypertensive effect in SH rats | | | |
|---|---|---|---|---|
| | Decreased % in blood pressure | | | |
| Example | i.p. | p.o. | | |
| No. | 30 mg/kg | 10 mg/kg | 30 mg/kg | 100 mg/kg |
| 1 | 24 | 8 | 16 | |
| 2 | 30 | 7 | 26 | |
| 3 | 14 | 11 | 27 | |
| 4 | 22 | | | |
| 5 | 16 | | | |
| 6 | 17 | 14 | 12 | |
| 7 | 27 | | 14 | |
| 8 | 14 | | 38 | |
| Hexamethonium | | | | 11 |
| Guanethidine | | | | 12 |

What is claimed is:

1. A compound having the formula,

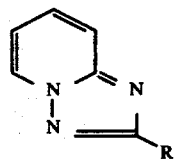

wherein R represents —CH=N—R$^1$
(wherein R$^1$ represents dimethylamino) and

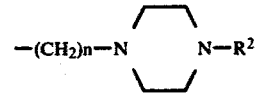

(wherein R$^2$ represents phenyl, 2-methoxyphenyl, benzyl, 2-chlorobenzyl and 2-pyridyl, and n represents 3 and 5), and the acid addition salts thereof.

2. 2-(N,N-Dimethylhydrazonomethyl)-s-triazolo[1,5-a]pyridine.

3. 2-[3-(4-Phenylpiperazino)propyl]-s-triazolo[1,5-a]pyridine.

4. 2-[3-(4-o-Methoxyphenylpiperazino)propyl]-s-triazolo[1,5-a]pyridine.

5. 2-[3-(4-Benzylpiperazino)propyl]-s-triazolo[1,5-a]pyridine.

6. 2-[3-(4-o-Chlorobenzylpiperazino)propyl]-s-triazolo[1,5-a]pyridine.

7. 2-[3-(4-Pryidin-2-ylpiperazino)propyl]-s-triazolo[1,5-a]pyridine.

8. 2-[5-(4-Phenylpiperazino)pentyl]-s-triazolo[1,5-a]pyridine.

9. 2-[5-(4-o-Methoxyphenylpiperazino)pentyl]-s-triazolo[1,5-a]pyridine.

10. 2-[3-(4-Phenylpiperazino)propyl]-s-triazolo[1,5-a]pyridine maleate.

11. 2-[3-(4-o-Chlorobenzylpiperazino)propyl]-s-triazolo[1,5-a]pyridine maleate.

* * * * *